US012605484B2

(12) United States Patent　(10) Patent No.: US 12,605,484 B2
Chiarelli　(45) Date of Patent: Apr. 21, 2026

(54) TWO-COMPONENT SYSTEM FOR THE THERAPEUTIC TREATMENT OF SKIN LESIONS AND PRODUCTION METHOD THEREOF

(71) Applicant: DTECH—SOCIETÀ A RESPONSABILITÀ LIMITATA, Maglie (IT)

(72) Inventor: Piero Chiarelli, Maglie (IT)

(73) Assignee: DTECH - SOCIETÀ A RESPONSABILITÀ LIMITATA, Maglie (IT)

( * ) Notice: Subject to any disclaimer, the term of this patent is extended or adjusted under 35 U.S.C. 154(b) by 501 days.

(21) Appl. No.: 17/600,913

(22) PCT Filed: Mar. 26, 2020

(86) PCT No.: PCT/IB2020/052851

§ 371 (c)(1),
(2) Date: Oct. 1, 2021

(87) PCT Pub. No.: WO2020/201940

PCT Pub. Date: Oct. 8, 2020

(65) Prior Publication Data

US 2022/0211902 A1　Jul. 7, 2022

(30) Foreign Application Priority Data

Apr. 3, 2019　(IT) ........................ 102019000005004

(51) Int. Cl.
*A61L 26/00*　(2006.01)

(52) U.S. Cl.
CPC ....... *A61L 26/0052* (2013.01); *A61L 26/0066* (2013.01); *A61L 26/0076* (2013.01); *A61L 26/008* (2013.01)

(58) Field of Classification Search
CPC . A61L 26/0052; A61L 26/0076; A61L 26/008
See application file for complete search history.

(56) References Cited

U.S. PATENT DOCUMENTS

2017/0015881 A1*　1/2017　Tanaka ................... C09J 133/26
2017/0157286 A1*　6/2017　Landolina ................ A61P 1/02

FOREIGN PATENT DOCUMENTS

CN　107823695 A　*　3/2018　............. A61L 15/20
KR　20140005322 A　*　3/2012
WO　WO-03063923 A1　*　8/2003　......... A61L 26/0066
WO　2013/071235　5/2013
WO　2014/181299　11/2014

OTHER PUBLICATIONS

Lee, B. et al. "Gelation of an alginate film via spraying of calcium chloride droplets", Chem Engineering Science, 183, 2018, 1-12.*
O. Catanzano, et al., "Spray-by-spray in situ cross-linking alginate hydrogels delivering a tea tree oil microemulsion", European Journal of Pharmaceutical Sciences, vol. 66, Sep. 30, 2014, pp. 20-28.
I. Gibas, et al., "Synthetic polymer hydrogels for biomedical applications", Chemistry & Chemical Technology, vol. 4, No. 4, Jan. 1, 2010, pp. 297-304.
International Search Report and Written Opinion of the ISA for PCT/IB2020/052851 dated Jul. 15, 2020, 10 pages.

* cited by examiner

*Primary Examiner* — Gina C Justice
(74) *Attorney, Agent, or Firm* — NIXON & VANDERHYE

(57) ABSTRACT

A two-component system for the therapeutic treatment of skin lesions includes two components. A first component is an aqueous gel. A second component, called cross-linker, is an aqueous solution. The first component includes at least one biocompatible polymer, at least one polyacid or a salt thereof and characterized in that at least one preservative substance, at least one pharmacologically active substance can be present and in that the second component consists of a saline solution including calcium chloride, magnesium chloride and zinc chloride. A method of use involves the prior application of the first component, in the form of aqueous gel in a fluid-viscous state on the skin of a patient, then spraying with the second component as an aqueous solution, causing the formation in situ of a film of rubbery consistency and in that the rubbery film can be removed by washing the skin with water.

11 Claims, No Drawings

TWO-COMPONENT SYSTEM FOR THE THERAPEUTIC TREATMENT OF SKIN LESIONS AND PRODUCTION METHOD THEREOF

This application is the U.S. national phase of International Application No. PCT/IB2020/052851 filed Mar. 26, 2020 which designated the U.S. and claims priority to IT patent Application No. 102019000005004 filed Apr. 3, 2019, the entire contents of each of which are hereby incorporated by reference.

BACKGROUND OF THE INVENTION

Field of the Invention

The present patent application for invention relates in general to the medical health sector and more specifically to the branch of dermatology, surgery and cardiac surgery. More specifically, the present invention falls within the field of therapeutic treatments for the prevention and treatment of infections resulting from injuries of the skin or dermis, as well as from burns and accidental causes, from prolonged hospital stay and/or for the healing of surgical sutures.

Description of the Related Art

As is known, any alteration of the skin surface caused by a pathological, traumatic or environmental event is called a skin lesion.

The intact skin is colonized by numerous bacterial species, defined as "resident bacterial flora", which exhibits a competitive action towards other bacterial species that want to implant themselves. In most cases, skin lesions have a rapid course towards healing, but in some patients, despite medical and nursing care, the course is particularly long and complex and does not always evolve into healing. In the case of wounds such as extensive surgical sutures and burns, the massive presence of bacterial contamination can compromise the patient's health and lead, in extreme cases, even to death from sepsis. Consequently, these injuries have a negative impact on physical and mental health and more generally on the quality of life of patients, they cause prolonged hospitalizations, the consumption of important resources with repercussions on the health system both in organizational and economic terms.

The risk of infection of a chronic skin lesion is linked to the resistance of the host and the characteristics of the bacteria, to the charge and virulence. In reality, all skin lesions are contaminated, but this condition is characterized by the presence of non-replicating or reduced growth microorganisms, with ease of the healing process. However, it is possible that they pass to successive stages characterized by an increase in the bacterial load, which tends to replicate faster where the host is no longer able to maintain a balance between aggressive and defensive factors, causing an extension of the lesion with evident delay in the healing process. Finally, the condition of infection can be reached, characterized by intense cell replication and blocking of the cell repair process. In this case, even the massive loss of body fluids, with consequent dehydration of the patient, is a complication that aggravates the clinical picture and must be avoided. In cases of bedsores, compression of the tissues hinders their normal physiology, causing necrosis over time. In this case, it is important to associate the local administration of factors stimulating tissue regrowth and maintaining its optimal state of hydration.

Current techniques to assist wound healing essentially consist of covering the wound itself with bandages, which often require replacement both for contamination and for periodically adding medicaments, antiseptics and antibiotics, in order to prevent bacterial contamination. However, the use of bandages is often difficult and painful for the patient, having the drawback that they must be removed, causing pain and possibly irritation and the exacerbation of the patient's injury. In the case of bedsores, adhesion to sheets or clothing can generate, for similar reasons, serious problems and the application of creams must be repeated very frequently as they are mechanically removed from the bandage.

In general, in order to effectively treat a wound, it is necessary first to create an efficient barrier from the outside, in order to maintain the humidity of the tissue and avoid an excessive loss of fluids, allowing the exchange of gases such as oxygen and carbon dioxide. The production of a bacteriostatic and bioadhesive action of the barrier to prevent the entry of bacteria and a prolonged and continuous release of antiseptics, anti-inflammatories, antibiotics and/or factors stimulating tissue regrowth or coagulation factors, is therefore a fundamental condition for maintaining conditions suitable for healing the same lesion. Another necessity consists in having a barrier with good mechanical and elastic features, which can house sensors and indicators therein for detecting the wound healing status or the onset of infections.

Finally, a further feature in the treatment of skin lesions is that of creating a barrier of good durability, with non-stick outer surface, with high resistance and easily removable. In order to overcome these and other drawbacks of the products currently on the market, the inventors have provided a combined product for clinical use in dermatology, surgery and cardiac surgery, characterized by forming in situ a stable elastic film, permeable to gas and breathable.

Another object of the present invention is to provide a system for dermatological use, capable of containing body fluids avoiding dehydration of the tissues and which is easily removable by means of a simple washing with water.

A more particular object is to provide a bioadhesive system for dermatological use, capable of releasing over time active ingredient molecules capable of exerting a local or systemic effect in the human or animal organism. In particular, the object of the present invention is precisely to release pharmacologically active substances such as antiseptics, anti-inflammatories, regrowth factors, coagulation factors, antibiotics and so on.

Other advantages of the invention will become apparent from the detailed description of an embodiment thereof provided by way of non-limiting example, illustrated below.

SUMMARY OF THE INVENTION

The present patent application for industrial invention aims to describe and claim a two-component system forming a bioadhesive system for the therapeutic treatment of skin lesions in general, as well as wounds, burns, bedsores, ulcers and so on, consisting of a first component in the form of aqueous gel, called base gel, a second component, called cross-linking component, in the form of aqueous saline solution.

More specifically, said first component consists of a mixture of a biocompatible polymer, a polyacid or a salt thereof and at least one preservative and one or more pharmacologically active substances as well as antiseptics, anti-inflammatories, regrowth factors, coagulation factors and antibiotics for dermatological use in aqueous solution.

Said second component, on the other hand, consists of an aqueous solution of a salt of a bivalent, trivalent or multivalent cation.

As regards the clinical use of said inventive two-component system, it must be reported that this involves a preventive application thereof on the skin of a patient who needs aseptic conditions and protection from bacterial infections and/or damage from of fragments of dirt, so as to cover it evenly and adapt to its shape and to the affected body site. Only subsequently, said aqueous gel, present in a fluid-viscous state, is sprayed with the second component in the form of an aqueous solution, inducing the formation in situ of the inventive rubbery film. Said inventive film once formed has a porosity of less than 10 microns and forms a barrier which prevents the passage of bacteria and spores, allowing gases such as oxygen, carbon dioxide, nitrogen and water vapor to pass through, retaining the water while permitting its transpiration, with a shear elastic modulus greater than 1,000,000 Newtons per square meter and an elongation at break not less than 100%.

This solution according to the present invention constitutes an optimal compromise, in that said rubbery gel film is advantageously capable of carrying out various actions.

The adhesion process of the polymer, in fact, involves the formation of an intimate contact between the surface of the lesion and the polymeric chains of the bioadhesive system, especially through the dehydration of the surface of the mucous membrane or of the exposed skin surface, followed by the formation of cross-linked secondary chemical bonds between these two surfaces, as well as hydrogen bonds.

Firstly, this situation creates a protective and bacteriostatic barrier action which, combined with a bioadhesive action in the application area, hinders the infiltration of bacteria and dirt fragments.

To all this the mucoadhesion process allows the drug carried to remain in close contact with the site of action or absorption for a prolonged time, resulting in an improvement of the pharmacokinetic profile of the active substance and, consequently, greater efficacy of the therapy and a possible reduction of side effects.

It should also be emphasized that this inventive means of forming the film allows it to adapt perfectly to any body site, allowing it to perform its function with ease and continuity.

Furthermore, the presence of polyvinyl alcohol gives the resulting film elasticity, rubbery solidity (with strong resistance to elongation and stress) and adhesive properties that allow the sealing action of the intervention sites and their protection from bacteria infiltration, allowing resistance to large stresses and also to exhibit anti-adhesive properties to external bandages.

A further fundamental aspect according to the present invention, alongside all the technical solutions described so far, but of particular relevance in the implementation of the invention, starts from the fact that the wound environment is dynamic and the healing rate can be improved with the administration of therapy at the right time. This approach therefore requires real-time monitoring of the wound environment, which can always be related to the bioadhesive action of said film. In fact, as will be seen in the detailed description, said two-component system could act as a real support for sensors and chemical indicators, monitoring the state of the wounds in real time and allowing an appropriate response for that specific moment.

Other features of the present invention are described in the following detailed description of one or more specific embodiments thereof.

DESCRIPTION OF THE PREFERRED EMBODIMENTS

A preferred embodiment of the present invention will now be described in detail also with reference to the production method described below.

A first aspect of the present invention consists in that said two-component system for the therapeutic treatment of skin lesions as well as wounds, burns, bedsores, ulcers consists of two components, a first component in the form of aqueous gel and a second component in the form of aqueous solution.

More specifically, said first component is made up of at least one biocompatible polymer, at least one polyacid or a salt thereof and one or more preservative and pharmacologically active substances. The values of the optimal concentration will also be reported below, in order to obtain an effective system capable of guaranteeing the formation of a resistant film, of good elasticity, with adequate porosity for the passage of gases, as well as the oxygen and carbon dioxide but such as to prevent the passage of bacteria.

In detail, a preferred embodiment of the present invention is characterized in that the biocompatible polymer is polyvinyl alcohol and has a molecular weight in the range of 10 to 1,000,000 and more preferably a molecular weight greater than 10,000, at a concentration with respect to said first component between 0.001-30% w/w and preferably between 1%-10% w/w.

As far as the polyacid is concerned, this is represented by the polyacrylic acid and sodium alginate taken alone or in association, wherein said polyacrylic acid with a molecular weight between 10 and 5,000,000 and preferably equal to 400,000 is present at a concentration with respect to said first component between 0.01-10% w/w and more preferably between 2-4% w/w and wherein the sodium alginate is present at a concentration with respect to said first component comprised between 0-5% w/w and preferably equal to 1.5% w/w with a viscosity ranging between 50 and 2000 cp at 20° C.

As far as the pharmaceutically active molecules and the preservatives present in the first inventive compound are concerned, these are manifold and as specified below they belong to various pharmaceutical categories.

In particular, a preferred embodiment of the present invention provides that the antibiotic for dermatological use is selected from the group consisting of metronidazole, metronidazole benzoate, any antibiotic belonging to the nitroimidazole family, doxycycline, any antibiotic belonging to the tetracycline family, amoxicillin also associated with clavulonic acid and any antibiotic belonging to the penicillin family, rifaximin and any antibiotic belonging to the rifamicin family, neomycin, mupirocin and any combination thereof, at a concentration of the antibiotic with respect to said first component comprised between 0.01-70% w/w and more preferably between 0.5-30% w/w.

In said preferred embodiment, the antiseptic is selected from the group comprising chlorhexidine gluconate, iodine, silver ions and any combination thereof, at a concentration with respect to said first component comprised between 0.0001-10% w/w, more preferably between 0.002-4% w/w.

In said preferred embodiment, the anti-inflammatory is selected from the group comprising acetylsalicylic acid and/or flurbiprofen and any combination thereof, at a concentration with respect to said first component comprised between 0.001-30% w/w, more preferably between 0.5-10% w/w.

In said preferred embodiment, the regenerative factor of the tissues is hyaluronic acid, at a concentration with respect to said first component comprised between 0.001-30% w/w and more preferably between 0.01-2% w/w.

In said preferred embodiment, the regenerative factor contained in said first component is selected from the group comprising hyaluronic acid and/or a sodium salt thereof, retinol, vitamin A, vitamin C, vitamin D, vitamin E, biotin, linoleic acid, arachidonic acid, co-enzyme Q10, oxygen, hydrogen peroxide, or other oxygen-producing compounds and any combination thereof.

In said preferred embodiment, the local coagulant factor is selected from the group comprising Vitamin K, protamine, fibrinogen, prothrombin, calcium, proaccelerin, accelerin, proconvertine, anti-hemophilic A factor, Christmas factor, tissue III factor, Stuart power factor, plasmatic antecedent of thromboplastin, Hageman factor, fibrin stabilizing factor or any combination thereof, at a concentration with respect to said first component comprised between 0.001-4% w/w, more preferably between 0.2-2% w/w.

In said preferred embodiment, the first component contains preservatives selected from the group comprising the members of the paraben class or the group of propyl paroxybenzoate and methyl paroxybenzoate or any combination thereof.

As regards instead said second component present in the aforementioned preferred embodiment, this is constituted by a saline solution wherein the cation is bivalent, trivalent or has higher valence, wherein said salt is selected from the group comprising chlorides, iodides and wherein preferably said salt is selected from the group comprising calcium chloride, magnesium chloride and zinc chloride at the concentration comprised between 0.001 moles and the solution saturation concentration.

By way of non-limiting example, a particularly preferred composition according to the present invention is constituted by the presence of the first component in the form of a mixture in aqueous solution of polyvinyl alcohol with a molecular weight of about 90,000 at a concentration of about 2% w/w, of sodium alginate at a concentration of about 2% w/w, of the silver ion at a concentration of about 1% w/w and/or of chlorhexidine gluconate at a concentration of about 2-4% and of flurbiprofen at a concentration of about 5% w/w and consists of the presence of the second component in the form of a saline solution of calcium chloride, with a concentration preferably comprised between 0.001 and 10 M.

However, although up to now the case has been considered in which pharmaceutically active substances are included among the constituents in the first component, this should not be considered limitative for the present invention, since said inventive therapeutic system can also contain substances for cosmetic, nutraceutical use and micronutrients, in particular to assist tissue regeneration processes. Therefore the fields of application of the release systems of the invention are the medical, pharmaceutical, cosmetic and cosmeceutical (cosmetic for therapeutic purposes) and nutraceutical fields. As already mentioned above, an approach to detecting the dynamic environment of a skin lesion requires the presence at this of chemical, physical or biological sensors, as well as sensors for temperature, pH value, bacterial load value, etc. This situation is implemented by allowing said inventive two-component system to integrate or act as a support for common chemical, physical or biological sensors and indicators as specified below.

For this purpose, the possibility is envisaged that said inventive system acts as a support for at least one device for detecting the temperature, the pH value, the ionic concentration, the saline concentration, the oxygen concentration, the perfusion of oxygen in the tissues, the concentration of carbon dioxide or any combination thereof.

Still in the light of the foregoing, the presence is provided, within the composition of said first inventive component of a fluorescent substance for the detection of bacterial strains selected from the group comprising the green fluorescent protein (GFP), fluorescein, dichlorofluorescein, Dylight Fluor, or a combination thereof.

Another feature within the scope of the concept just described is that said inventive system provides for the presence within the composition of the first component of colorimetric indicators of the state of the skin lesion for the indication of the pH value, of the oxidoreductive characteristics, of the salinity, of the oxidoreductive activity and of the dissolved gases and such indicator is selected from among the group comprising bromothymol blue, thymol blue, methyl violet, basic violet 3, methyl yellow, methyl orange, bromophenol blue, bromocresol green, methyl red, phenol red, cresol red, 1-naphtholphthalein, phenolphthalein, thymolphthalein, bromocresol violet, trinitrotoluene, ferroin, N-phenylanthranylic acid, naphthyl black, 2,2'-bipyridine (complex with Ru), nitrophenanthroline (complex with Fe), N-phenylanthranylic acid, 1,10-phenanthroline (complex with Fe), N-ethoxychrisoidine, 2,2'-(complex with Fe), 5,6-dimetylphenanthroline (complex with Fe), o-dianisidine, sodium diphenylaminesulfonate, diphenylbenzidine, diphenylamine, viologen, 2,6-dibromophenol-indophenol, o-cresol-indophenol, thionin (or "Lauth violet"), methylene blue, indigotetrasulfonic acid, indigotrisulfonic acid, carmine indigo (indigosulfonic acid), indigomonosulfonic acid, phenosafranine acid, safranine T, basic red 5, or any combination thereof.

In a second aspect, the present invention relates to a method of producing the preferred composition described above. However, the following examples, which relate to the preparation, characterization and use of the product according to the invention, are provided for illustrative purposes only and are not intended to limit in any way the scope of the present invention as defined by the appended claims.

Example 1: Preparation

The base gel (first component) was obtained by dissolving polyvinyl alcohol, with a molecular weight of 90,000, in water at a concentration of 4% w/w. The solution was stirred until a homogeneous solution was obtained, after which hyaluronic acid was added at a concentration of 0.5% w/w, flurbiprofen at a concentration of 5% w/w and high molecular weight sodium alginate at the concentration of 2% w/w. Finally, silver chloride was added to the whole at a concentration of 1% w/w and chlorhexidine gluconate at a concentration of 2% w/w. The saline solution consists of an aqueous solution of 1 molar calcium chloride.

Example 2: Application

The gel prepared according to example 1 was applied to skin lesions and then sprayed with calcium chloride prepared according to example 1, by means of a spray nebulizer.

Example 3: Characterization of the Elastic Film

The rubbery film, obtained with the process described in example 1, is characterized by elasticity and release capacity of flurbiprofen, silver ions, chlorhexidine gluconate and hyaluronic acid contained therein. Measurements of the elastic elongation at break in gel samples were made, which was greater than 100%. The release of flurbiprofen, silver ions and hyaluronic acid was longer than 7 days.

Example 4: Alternative Preparation

The base gel (first component) was obtained by dissolving polyvinyl alcohol, with a molecular weight of 90,000, in water at a concentration of 4% w/w. The solution was stirred until a homogeneous solution was obtained, after which hyaluronic acid was added at a concentration of 0.5% w/w, polyacrylic acid at a concentration of 0.5% w/w, sodium alginate, with specific viscosity of 4,000 cp, at a concentration of 1.5% w/w. Finally, silver chloride was added to the whole at a concentration of 1% w/w, chlorhexidine glucon-ate at a concentration of 2% w/w and acetylsalicylic acid at a concentration of 10% w/w.

The cross-linker (second component) capable of trans-forming the gel into a solid having the consistency of a soft rubber, consists of an aqueous solution of 1 molar calcium chloride.

Example 5: Alternative Preparation for Inserting Physical Sensors

The base gel (first component) was obtained by dissolving polyvinyl alcohol, with a molecular weight of 90,000, in water at a concentration of 10% w/w. The solution was stirred until a homogeneous solution was obtained, after which polyacrylic acid was added at a concentration of 4% w/w which was also dissolved by stirring the solution. The final homogeneous solution, after inserting and positioning the temperature and oxygen sensors, was dried in a stove at 40° C. in the presence of dehydrating salt for 24 hours. The final rubbery film containing the sensors was cross-linked at 80° C. for one hour. The solid-elastic film thus obtained is adhered to the skin above and around the wound or suture using as adhesive the gel prepared according to example 1 and applied according to example 2.

The invention claimed is:

1. A two-component system for use in the therapeutic treatment of skin lesions, comprising: a first component in the form of an aqueous gel and a second component, being a cross-linking agent, in the form of an aqueous solution, wherein said first component comprises at least one biocompatible polymer, and at least one polyacid or a salt thereof; and said second component comprises a saline solution con-taining a bivalent, trivalent or higher valence cation; wherein said biocompatible polymer is polyvinyl alcohol with a concentration with respect to said first component between 0.001-30% w/w and with a molecular weight from 10,000 to 1,000,000;

said polyacid is at least one member selected from the group consisting of polyacrylic acid and sodium alg-inate;

said polyacrylic acid having a molecular weight between 400,000 and 5,000,000 and having a concentration with respect to said first component between 0.01-10% w/w;

said sodium alginate when present having a concentration with respect to said first component of at most 5% w/w, with a viscosity ranging between 50 and 2000 cp at 20° C.; and wherein application of the first component, in the form of an aqueous gel in a viscous fluid state on the skin of a patient, followed by spraying with the second component in aqueous solution form, induces in situ forma-tion of a film with rubbery consistency and wherein said rubbery film can be removed by washing of the skin with water.

2. The two-component system according to claim 1, wherein at least one preservative substance is present in the first component as well as at least one pharmacologically active substance.

3. The two-component system according to claim 2, wherein the at least one pharmacologically active substance is selected from the group consisting of antibiotics, antisep-tics, anti-inflammatory agents, tissue regenerative factors, local coagulant factors and preservative compounds.

4. The two-component system according to claim 3, wherein:

said antibiotics are selected from the group consisting of metronidazole, metronidazole benzoate, antibiotics belonging to the family of nitroimidazoles, doxycy-cline, antibiotics belonging to the family of tetracy-clines, amoxicillin also associated with clavulanic acid and antibiotic belonging to the family of penicillins, rifaximin and antibiotics belonging to the family of rifamycins, neomycin, mupyrocin and combinations thereof;

said antiseptics are selected from the group consisting of chlorhexidine gluconate, iodine, silver ions and com-binations thereof;

said tissue regenerative factors are selected from the group consisting of hyaluronic acid, a sodium salt thereof, retinol, Vitamin A, Vitamin C, Vitamin D, Vitamin E, biotin, linoleic acid, arachidonic acid, co-enzyme Q10, oxygen, oxygenated water, other com-pounds developing oxygen and combinations thereof;

said local coagulant factors are selected from the group consisting of Vitamin K, protamine, fibrinogen, pro-thrombin, calcium, proaccelerin, accelerin, proconver-tine, anti-hemophilic A factor, Christmas factor, tissue III factor, Stuart power factor, plasmatic antecedent of thromboplastin, Hageman factor, fibrin stabilizing fac-tor and combinations thereof;

said preservative compounds are a paraben, propyl paraoxybenzoate, methyl paraoxybenzoate or a combi-nation thereof.

5. The two-component system according to claim 1, wherein said second component comprises a saline solution wherein the cation is at least bivalent, and wherein said salt is selected from the group consisting of calcium chloride, magnesium chloride and zinc chloride at the concentration comprised between 0.001 moles and a solution saturation concentration.

6. The two-component system according to claim 1, wherein said first component further comprises at least one of the following components: fluorescent substances for the detection of bacterial strains, at least one colorimetric indi-cator for the indication of the pH value, of the oxidoreduc-tive characteristics within the gel, of the salinity, of the oxidoreductive activity and of the dissolved gases.

7. The two-component system according to claim 6, wherein: such fluorescent substance is selected from the group consisting of green fluorescent protein (GFP), fluo-rescein, dichlorofluorescein, Dylight Fluor, and combina-tions thereof; and such indicator is selected from the group consisting of bromothymol blue, thymol blue, methyl violet, basic violet 3, methyl yellow, methyl orange, bromophenol blue, bromocresol green, methyl red, phenol red, cresol red, 1-naphtholphthalein, phenolphthalein, thymolphthalein, bromocresol violet, trinitrotoluene, ferroin, N-phenylanthranylic acid, naphthyl black, 2,2'-bipyridine (complex with Ru), nitrophenanthroline (complex with Fe), N-phenylan-thranylic acid, 1,10-phenanthroline (complex with Fe), N-ethoxychrisoidine, 5,6-dimetylphenanthroline (complex with Fe), o-dianisidine, sodium diphenylaminesulfonate, diphenylbenzidine, diphenylamine, viologen, 2,6-dibrom-ophenol-indophenol, o-cresol-indophenol, thionin (or "Lauth violet"), methylene blue, indigotetrasulfonic acid, indigotrisulfonic acid, carmine indigo (indigosulfonic acid), indigomonosulfonic acid, phenosafranine acid, safranine T, basic red 5, and combinations thereof.

8. The two-component system according to claim 1, wherein said system when in contact with the skin or mucous membrane acts as a support for at least one device for detecting the temperature, the pH value, the ionic concentration, the saline concentration, the oxygen concentration, the perfusion of oxygen in the tissues, the concentration of carbon dioxide or a combination thereof.

9. The two-component system according to claim 1, wherein said film with rubbery consistency, once formed, has a porosity smaller than 10 microns, in that it has a shear elastic modulus greater than 1,000,000 Newtons per square meter and in that it has an elongation at break not less than 100%.

10. The two-component system according to claim 1, wherein said film performs a bioadhesive activity, in that the bioadhesion process allows the transported active principle to remain in close contact with the site of action or of absorption for a prolonged time period, obtaining an improvement of the pharmacokinetic profile of the active principle itself and in that a water-impermeable barrier is attained which prevents the passage of bacteria and spores and which is permeable to gases such as oxygen, carbon dioxide, nitrogen and water vapor.

11. The two-component system according to claim 1, wherein the first component comprises at least one of cosmetic, nutraceutical and micronutrients, for assisting tissue regeneration.

* * * * *